(12) United States Patent
Kennedy et al.

(10) Patent No.: US 7,404,490 B2
(45) Date of Patent: Jul. 29, 2008

(54) CONTINUOUS PARTICLE SEPARATION APPARATUS

(75) Inventors: David J. Kennedy, Greenville, IN (US); Eric W. Taylor, Greenville, IN (US); John C. Vellinger, Floyds Knobs, IN (US)

(73) Assignee: SHOT, Inc., Greenville, IN (US)

( * ) Notice: Subject to any disclaimer, the term of this patent is extended or adjusted under 35 U.S.C. 154(b) by 221 days.

(21) Appl. No.: 11/152,975

(22) Filed: Jun. 15, 2005

(65) Prior Publication Data

US 2007/0000814 A1    Jan. 4, 2007

(51) Int. Cl.
*B03B 5/62* (2006.01)
*B03B 5/00* (2006.01)

(52) U.S. Cl. .................. 209/208; 209/210; 137/561
(58) Field of Classification Search .......... 209/208, 209/210; 137/561
See application file for complete search history.

(56) References Cited

U.S. PATENT DOCUMENTS

| | | | |
|---|---|---|---|
| 4,141,809 A | 2/1979 | Aitchison et al. | |
| 5,039,426 A * | 8/1991 | Giddings | 210/695 |
| 5,968,820 A | 10/1999 | Zborowski et al. | |
| 6,120,735 A * | 9/2000 | Zborowski et al. | 422/73 |
| 6,312,910 B1 | 11/2001 | Vellinger et al. | |
| 6,365,050 B1 * | 4/2002 | Cauchon | 210/635 |
| 6,467,630 B1 * | 10/2002 | Zborowski et al. | 209/459 |
| 6,623,984 B1 | 9/2003 | Fleischman et al. | |
| 6,688,473 B2 * | 2/2004 | Franzreb et al. | 209/39 |
| 6,699,669 B2 | 3/2004 | Vellinger et al. | |

FOREIGN PATENT DOCUMENTS

WO    9838293    9/1998

OTHER PUBLICATIONS

Fuh, et al., "Hydrodynamic Characterization of SPLITT Fractionation Cells," Separation Science and Technology, 30(20), pp. 3861-3876, Marcel Dekker, Inc., 1995.
Hoyos, et al., "Pulse-Injection Studies of Blood Progenitor Cells in a Quadropole Magnetic Flow Sorter," J. Separation Science and Technology, 37(4), 1-23. 2002.
Hoyos, et al., "Study of Magnetic Particles Pulse-Injected Into an Annular SPLITT-Like Channel Inside a Quadrupole Magnetic Field," J. Chromatogr., A, 903 (1-2), 99-116, 2000.

(Continued)

*Primary Examiner*—Patrick Mackey
*Assistant Examiner*—Terrell Matthews
(74) *Attorney, Agent, or Firm*—Robert H. Eichenberger; Eric L. Killmeier; Middleton Reutlinger

(57) ABSTRACT

The present invention relates to an improved apparatus and method for assembly for a cylindrical split-flow thin separation channel that is capable of continuously separating particles of interest from a suspension flowing through the channel. The apparatus provides better precision in the separation process by providing better flow characteristics at the inlet, outlet, and in the zone of separation. Splitter surfaces are provided that match the calculated theoretical Inlet Splitter Surface (ISS) and Outlet Splitter Surface (OSS). A flow distributor diverts the inlet carrier flow into a stable, circumferentially uniform, laminar annular flow. The design enables manufacturing and assembly methods to ensure precise alignment of the components to further improve the flow profiles within the separation channel and to ensure repeatability device-to-device.

22 Claims, 17 Drawing Sheets

OTHER PUBLICATIONS

Lara et al., "Enrichment of Rare Cancer Cells Through Depletion of Normal Cells Using density and Flow-Through, Immunomagnetic Cell Separation," Experimental Hematoloty 32, pp. 891-904, Elsevier, Inc., 2004.

Lara et al., "Negative Depletion Cell Sorting Using a Quadrupole Magnetic Cell Sorter," European Cells and Materials, vol. 3. Supple. 2, pp. 62-64. 2002.

McCloskey, et al., "Magnetophoretic Mobilities Correlate to Antibody Binding Capacities," Cytometry. vol. 40, Issue 4, pp. 307-315, Apr. 2000, Wiley-Liss, Inc.

Moore, et al., "Progenitor Cell Isolation with a High-Capacity Quadrupole Magnetic Flow Sorter," J. Magn. Magn. Mater. 225 (1-2): 277-284. 2001.

Myers, "Overview of Field-Flow Fractionation," Journal of Microcolumn Separations, vol. 9, Issue 3, pp. 151-162, Jan. 1997, John Wiley & Sons, Inc.

Nakamura, et al., "Separation of a Breast Cancer Cell Line from Human Blood Using a Quadrupole Magnetic Flow Sorter," Biotechnol. Prog. 17, pp. 1145-1155, 2001.

Sun, et al., "Continuous, Flow-Through Immunomagnetic Cell Sorting in a Quadrupole Field," Cytometry 33, pp. 469-475, Wiley-Liss, Inc., 1998.

Williams, et al., "Flow Rate Optimization for the Quadrupole Magnetic Cell Sorter," Analytical Chemistry, 71:3799-3807, 1999.

Williams, et al., "The Potential of Quadrupole magnetic Field-Flow Fractionation for Determining Particle Magnetization Distributions," European Cells and materials, vol. 3, Supple. 2, pp. 203-205, 2002.

Williams, et al., "Splitter Inperfections in Annular Split-Flow Thin Separation Channels: Effect on Nonspecific Crossover," Analytical Chemistry, vol. 75, No. 6, Mar. 15, 2003, pp. 1365-1373.

Zborowski, et al., "Continuous Cell Separation Using Novel Magnetic Quadrupole Flow Sorter," Journal of Magnetism and Magnetic Materials, 194, pp. 224-230, 1999.

Zhang, et al., "General Theory for Flow Optimisation of Split-Flow Thin Fractionation" Journal of Chromatography A., 1010 pp. 87-94, Elsevier, Inc., 2003.

* cited by examiner

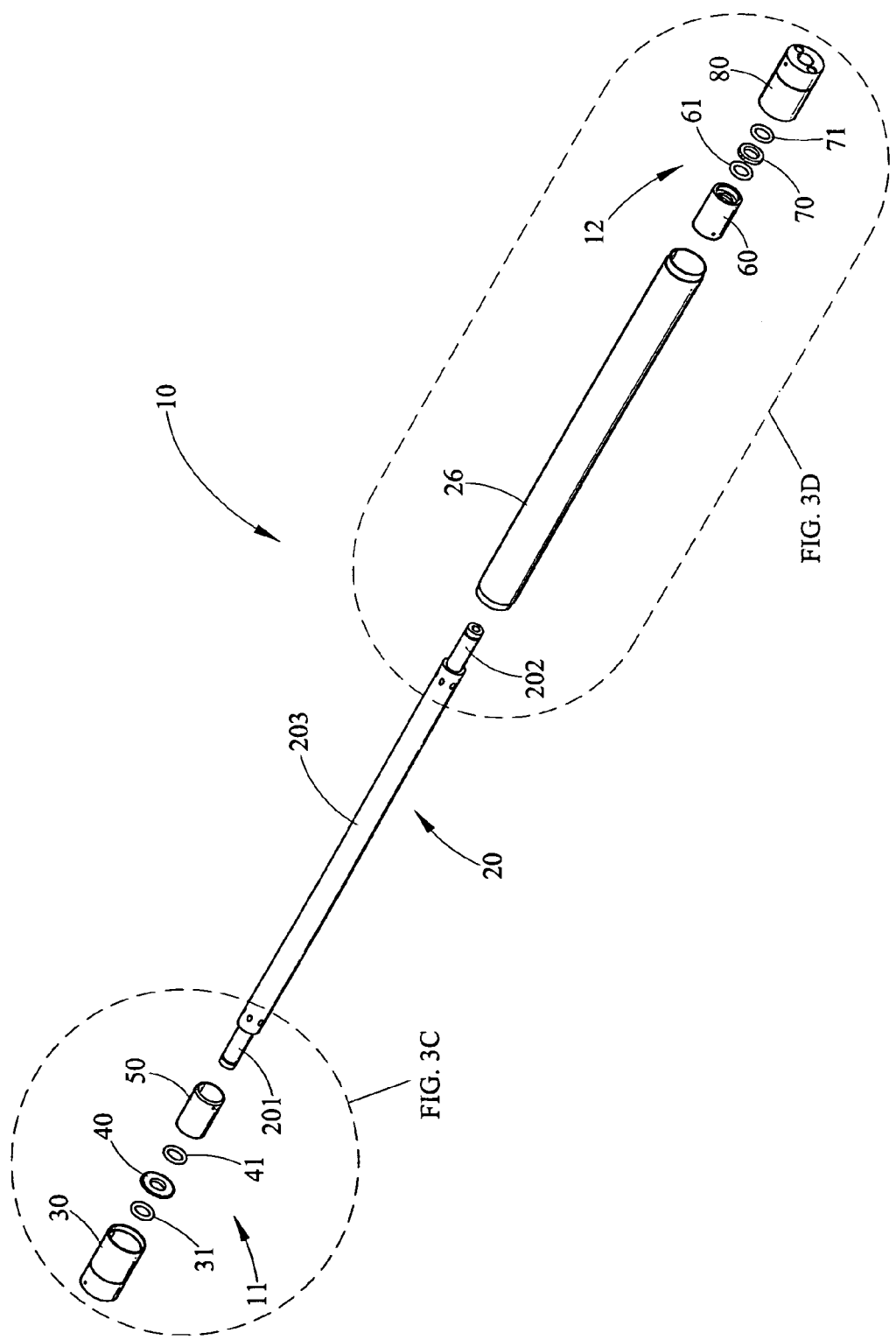

CONTINUOUS PARTICLE SEPARATION APPARATUS

BACKGROUND OF THE INVENTION

1. Field of the Invention

The present invention relates generally to an annular flow channel for maintaining uniform flow in the channel and for separating cells and particles in a radial force field.

2. Background

In general, particle separation devices take a variety of structures, depending upon the particles to be separated and the separation method to be employed. Particle separation devices separate particle populations into fractions of interest from a suspension and/or other types of particles. The principal method of operation of early particle separation devices relied on a particle's physical parameters to distinguish it from a suspension and/or other types of particles. Examples of these bulk separation techniques include filtration (which is based on particle size), and centrifugation (which is based on particle density and size). These techniques are effective as long as the particle population of interest is significantly different, with respect to size or density, from the suspension and/or the other particles in the population. Additional examples relate to multistage magnetically assisted separation technologies (MAGSEP), as disclosed in Vellinger, et al. U.S. Pat. Nos. 6,312,910 and 6,699,669.

As a subset of bulk separating, continuous separation techniques also exist. The continuous separation of particles in flowing solution requires a well-defined and well-controlled fluid flow pattern. Typically, continuous particle separation devices employ rectangular separation channels. The rectangular geometry of such separation channels provides several advantages including, for example, ease of manufacture, ease of control of fluid flows inside the channels, and ease of design and implementation of forces that drive the separation.

However, rectangular separation channels also suffer from a drawback known as the sidewall effect. The sidewall effect distorts the fluid flow pattern at the side walls of the rectangular separation channel and, hence, adversely affects the performance of the sorting device such as, for example, its resolving power. Therefore, it is desirable to provide methods and devices for separating particles that do not suffer from sidewall effects and can employ any one of a diverse number of separation forces.

Development in the art stemmed from the evolution of various Field-Flow Fractionation (FFF) techniques, as generally discussed in Myers, "Overview of Field-Flow Fractionation," Journal of Microcolumn Separations, vol. 9, issue 3, pages 151-162, January 1997, John Wiley & Sons, Inc., the entire disclosure of which is incorporated by reference herein. In FFF, a force field is directed perpendicularly across a laminar flow in order to focus particles into narrow bands based on a particular physical characteristic (such as size, molecular weight, charge, etc.) for analysis. Modifying the FFF technique by adding two additional flow streams and an inlet and outlet splitter surface effectively creates a split-flow thin separation channel. This channel allows the operator to fractionate the sample based on a physical characteristic and collect the positively and negatively selected fractions for further analysis or utilization.

Several rectangular embodiments of split-flow thin separation channels exist that attempt such separation using various driving forces including (but not limited to) gravitational, electrokinetic, thermal diffusion, centrifugation, and magnetophoretic. Recent embodiments of said channels utilize an approach where the negative impacts of the sidewall effects are eliminated by wrapping the separation channel around a cylinder and directing the flow paths parallel to the axis of the cylinder. The resulting geometry provides an annular separation volume that is contained between two concentric walls as disclosed in Aitchison et al. U.S. Pat. No. 4,141,809 and in Zborowski et al. U.S. Pat. Nos. 5,968,820 and 6,467,630B1. In one embodiment, a quadrupole magnet is used to generate a magnetic field with concentric B contour lines, thus providing a radial driving force in the annular separation volume that separates magnetic particles towards the outer wall of the annulus as disclosed in Zborowski et al. U.S. Pat. Nos. 5,968, 820 and 6,120,735. While these devices have seen some success in the laboratory, the prior art still contains drawbacks that have prevented the introduction of these devices into conventional practice.

In order for the split-flow thin separation process to provide a successful separation, it is essential that the sample and carrier solutions each form circumferentially consistent laminar flow profiles prior to engaging at the inlet splitter tip. Additionally, it is desirable that this flow profile be achieved for a wide range of inlet flow rates for both the sample and carrier solutions. Although prior art devices have produced a degree of circumferential distribution over some flow rate ranges, a need exists for better distribution over a wider range of flow rates. Furthermore, prior art devices suffer from an inability to be easily manufactured and assembled in an inexpensive, repeatable, and precise manner by, for example, injection molding techniques. A need exists for an apparatus that can provide multiple splitter diameters by machining and that can provide a single injection mold with simple interchangeable core pins that can manufacture splitters for a wide range of diameters and optimized flow regimes while being mechanically robust and not prone to breakage.

BRIEF SUMMARY OF THE INVENTION

The present invention provides solutions to these drawbacks. In one embodiment for continuously separating magnetic particles, clusters of particles and magnetically labeled biological cells, the device causes a suspension consisting of magnetic and non-magnetic particles to develop a circumferentially consistent laminar flow through an annular channel while a radial magnetic field gradient attracts particles outward in direct proportion to their net magnetic susceptibility.

This method of separation utilizes a channel with at least two inlets admitting sample suspension in an inner annulus and a carrier fluid in an outer annulus separated from the inner annulus by a cylindrical splitter. It also utilizes a channel with two outlets, one withdrawing magnetically attracted particles from an outer annulus and the other withdrawing non-attracted particles from an inner annulus separated from the outer annulus by a cylindrical splitter. Each of these inlets and outlets employs a novel geometric design that ensures that the flow at the splitter tip is a circumferentially consistent laminar flow distribution over a wide range of selected flow rates.

Preferably, the inlets and outlets have splitter surfaces that can be assembled in a rapid manner such that the splitter surfaces are concentric within a precise tolerance. Accordingly, it is an object of the present invention to provide components that sufficiently distribute the flows at the inlet and outlet splitters in a cylindrical split-flow thin separation channel to improve the separation process, and to do so utilizing an easily and precisely assembled device.

The sample inlet (herein referred to as the inlet-a fraction, or a') utilizes a novel design that has, as an input, a sample solution from a single tubing port, and has, as an output, a circumferentially consistent annular laminar flow of the sample solution. This is achieved by the novel geometry and integration of two components identified as the core and the inlet splitter.

The carrier inlet (herein referred to as the inlet-b fraction, or b') utilizes a novel design that has, as an input, one solution from one or more tubing ports and has, as an output, a circumferentially consistent annular laminar flow of the carrier solution. This is achieved by the novel geometry and integration of three components identified as the adaptor, flow distributor, and the inlet splitter.

The first fractional outlet (herein referred to as the outlet-a fraction, or a) utilizes a novel design that has, as an input, a circumferentially consistent annular laminar flow of depleted (i.e., negatively selected) solution and has, as an output, the depleted solution through a single tubing port. This is achieved by the novel geometry and integration of two components identified as the core and the outlet splitter.

The second fractional outlet (herein referred to as the outlet-b fraction, or b) utilizes a novel design that has, as an input, a circumferentially consistent annular laminar flow of enriched (i.e., positively selected) solution and has, as an output, the enriched solution from one or more tubing ports. This is achieved by the novel geometry and integration of two components identified as the adaptor and the outlet splitter.

The precision and ease of assembly for the innovative flow channel design relies on the novel use of the core as a means for properly aligning or self-fixturing that provides exacting alignment for all of the other components. Furthermore, the simple yet innovative method of integrating the adaptors, splitters, and flow distributor onto the core using basic cylindrical geometric principles results in a precisely aligned cylindrical split-flow thin channel.

BRIEF DESCRIPTION OF THE DRAWINGS

The present invention can take many physical embodiments and can assume many arrangements of components for carrying out the teachings of the invention, all of which may be appreciated by a person of skill in the art. The teachings of the present invention can be readily understood by considering the following detailed description of a preferred embodiment in conjunction with the accompanying drawings of said embodiment, in which:

FIG. 3B is an exploded perspective view of a flow channel according to an embodiment of the invention;

DETAILED DESCRIPTION OF THE PREFERRED EMBODIMENT

Figure 1:
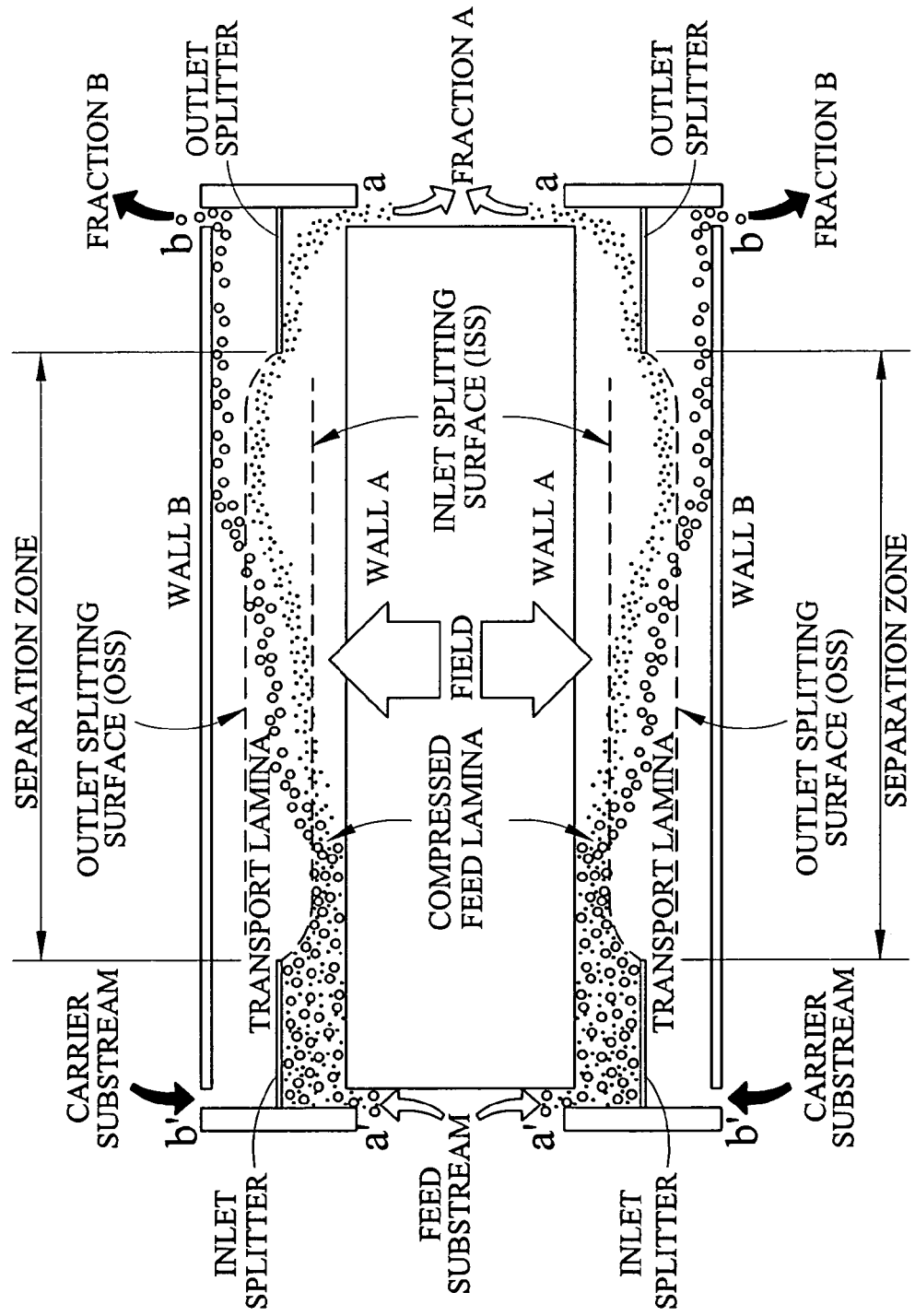
FIG. 1 is a sagittal section view of a hypothetical split-flow thin channel of the prior art showing the theoretical geometry and method of separation at its inlet and outlet ends.

While the present invention will be described more fully hereinafter with reference to the accompanying drawings in which particular embodiments and methods are shown, it is to be understood from the outset that persons of ordinary skill in the art may modify the invention herein described while achieving the functions and results of this invention. Sound engineering judgment may be used to modify various aspects and components of the invention without detracting from the broad, general teachings hereof. Accordingly, the description that follows is to be understood as illustrative and exemplary of specific embodiments within the broad scope of the present invention and not as limiting the scope of the invention. In the following descriptions, like numbers refer to similar features or like elements throughout.

Before discussing the particulars of the present invention, a brief summary of the basic theory of the split-flow thin separation technique will be presented. Prior art has extended the split-flow thin separation approach to flows in annular flow channels and axisymmetric, constant-force fields. The advantages of such novel flow and field configuration are the absence of the side-wall effects with the potential of an increased resolving power of the separation and a wider choice of the available force fields, in particular, the magnetic field. The theory of separation in an annular flow and a quadrupole magnetic field has been discussed by Zborowski et al U.S. Pat. No. 5,968,820.

The ability to immunomagnetically label selected cells to impart a magnetophoretic mobility to the cells in a suspension is useful for devices such as those according to the invention. Magnetophoretic mobility is defined as the characteristic motion of a particle induced by a magnetic field. The particle velocity, $u_m$, in an external magnetic field is defined as the product of the particle mobility (m) and the local field strength ($S_m$):

$$u_m = m \cdot S_m$$

The local field strength is defined as:

$$S_m = \frac{|\nabla B^2|}{2 \cdot \mu_o}$$

where $\nabla$ is the gradient operator, B is the magnetic field intensity (or the magnetic flux density), and $\mu_o$ is the magnetic permeability of free space ($4\pi \cdot 10^{-7}$ T·m/A).

Magnetophoretic cell separation using a device according to the invention relies on the value of the magnetophoretic mobility, m, of the immunomagnetically labeled cells. Cells have been found to exhibit a characteristic defined as Antibody Binding Capacity (ABC), which relates directly to the number of antibodies binding to the surface molecules on individual cells. By way of background, reference is made to McCloskey, et al., "Magnetophoretic Mobilities Correlate to Antibody Binding Capacities," Cytometry, vol. 40, issue 4, pages 307-315, April 2000, Wiley-Liss, Inc., the disclosure of which is incorporated herein by reference. In McCloskey, et al., it was shown that a linear relationship exists between magnetophoretic mobility and ABC, and the device can utilize this principle to isolate magnetically labeled particles not only based on a binary (magnetic vs. non-magnetic) feature, but even on a scalar feature based on the ABC value of the magnetically tagged cell. That is, cells can be selected on the basis of the quantity of surface antigenic sites.

FIG. 1 shows a conventional embodiment of a separation mechanism that is in the prior art. In FIG. 1, a standard flow channel configuration is presented showing internal wall (labeled A) and external wall (labeled B) of the annulus, field direction, sample inlet (a'), a carrier inlet (b'), negatively selected (i.e. depleted) fraction outlet (a), positively selected (i.e. enriched) fraction outlet (b), an Inlet Splitting Surface (ISS), and an Outlet Splitting Surface (OSS). In the prior art, the splitters were aligned with the middle of the separation zone, as shown in FIG. 1. Note in this configuration that the splitters are not aligned with the ISS and OSS, resulting in a "compression" of the inlet sample (a') just downstream of the splitter tip and an "expansion" of the positively selected (b) fraction just upstream of the splitter tip. The fluid shear created by the velocity differentials at these expansion and compression zones can result in undesirable mixing between the sample and carrier at the inlet, and between the two fractions at the outlet.

Figure 2:
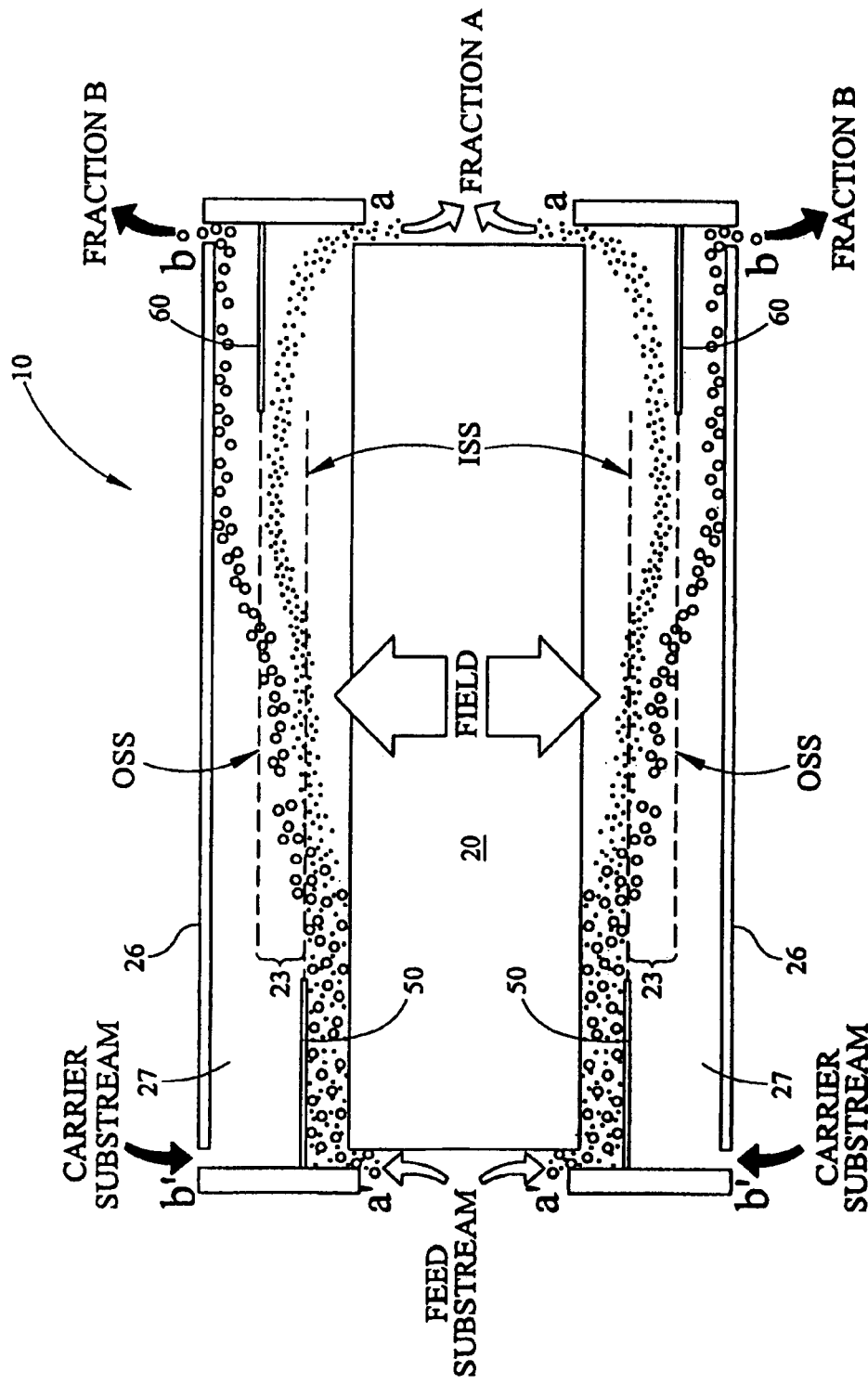
FIG. 2 is a sagittal section schematic of an improved flow channel showing an aligned geometric relationship between the inlet splitter and the Inlet Splitting Surface (ISS) and an aligned geometric relationship between the outlet splitter and the Outlet Splitting Surface (OSS)

The general notion of matching splitters to the ISS and the OSS was provided in Williams, et al., "Splitter Imperfections in Annular Split-Flow Thin Separation Channels: Effect on Nonspecific Crossover", Analytical Chemistry, vol. 75, no. 6, Mar. 15, 2003, pages 1365-1373. The present invention improves upon these theoretical concepts and provides a novel, functional, practical design that is fully operational and easily manufactured. FIG. 2 is a similar schematic showing an improved design according to an embodiment of the present invention. Note in the schematic that the inlet splitter 50 is aligned with the ISS and the outlet splitter 60 is aligned with the OSS, minimizing any "compression" or "expansion" effects and thereby minimizing fluid shear and turbulence impacts at the inlet and outlet. More details of the structures involved will be provided below.

A major advance is the ability to easily manufacture and install splitters in the inlet and outlet that are "tuned" for specific flow profiles, effectively optimizing the flow channel for a given set of flow rate requirements. Theoretical calculations for determining splitter geometry are noted in Williams et. al., "Flow Rate Optimization for the Quadrupole Magnetic Cell Sorter," Analytical Chemistry, vol. 71, no. 17, pages 3799-3807, September 1999, the disclosure of which is incorporated herein by reference. In the invention, two theoretical planes exist. These planes are identified as the Inlet Splitting Surface (ISS) and the Outlet Splitting Surface (OSS), and they develop during separations in a split-flow thin channel. The gap between the ISS and OSS is known as the transport lamina 23, and for a particle to be separated and eluted in the b fraction of the flow channel, the particle must cross the thickness of the transport lamina while it is in the annular flow volume. By setting the flow rates at the proper settings, it is possible to match the ISS to the inner diameter (and thus the diameter at the tip) of the inlet splitter, and likewise, the OSS can be matched to the inner diameter (and thus the diameter at the tip) of the outlet splitter. Any variation between the ISS and the inlet splitter, or the OSS and the outlet splitter, can result in increased fluid shear and potential turbulence at the fluid-fluid interface between the sample and carrier at the inlet and between the positively and negatively selected fractions at the outlet. Since turbulence in the channel reduces the precision of the separation process, the ability to calculate and tune the splitters at the manufacturing process to specific flow rates is a significant improvement over the prior art.

Moreover, as taught by Fuh, et al., "Hydrodynamic Characterization of SPLITT Fractionation Cells," Separation Science and Technology, 30(20), pp. 3861-3876, Marcel Dekker, Inc., 1995, tapering or chamfering the edges of the splitter suppresses vortex formation. Therefore, the splitters described herein preferably are tapered or chamfered in order to reduce mixing and maintain an absence of hydrodynamic mixing between laminae.

The theoretical position of the ISS can be calculated using the following system of equations, which are derived in more detail in Williams et. al. 1999 and are slightly modified for consistency of symbols with the previous equations and with equations presented later in this patent:

$$A_1 = (1 + \rho_i^2 - A_2)$$

$$A_2 = \frac{(1 - \rho_i^2)}{\ln\left(\frac{1}{\rho_i}\right)}$$

$$I_2[\rho_i, \rho_{ISS}] = [2\rho^2 - \rho^4 + 2A_2\rho^2 \ln\rho - A_2\rho^2]_{\rho_{ISS}}^{\rho_i}$$

$$R_i = \frac{I_2[\rho_i, \rho_{ISS}]}{A_1(1 - \rho_i^2)}$$

where $\rho_i$ is the ratio of the radius of the inside of the annular flow volume to the radius of the outside of the annular flow volume, and $\rho_{ISS}$ is the ratio of the radius of the ISS to the radius of the outside of the annular flow volume. Likewise, the OSS can be calculated by solving the following equation:

$$R_o = \frac{I_2[\rho_i, \rho_{OSS}]}{A_1(1-\rho_i^2)}$$

where $\rho_{OSS}$ is the ratio of the radius of the OSS to the radius of the outside of the annular flow volume. It can be determined from these equations that, for a fixed inner and outer diameter of the annular flow volume, the inlet splitter can be manufactured to match a specific inlet flow ratio, and likewise, an outlet splitter can be manufactured to match a specific outlet flow ratio.

Figure 3A:
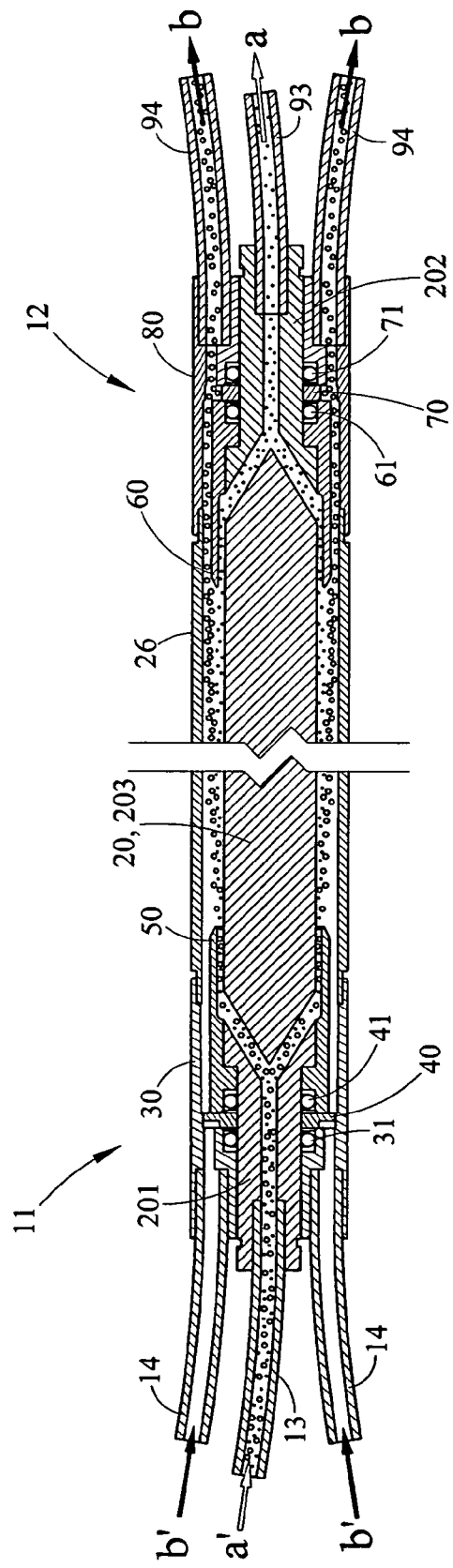
FIG. 3A is a sagittal section view of the assembled flow channel.
Figure 3C:
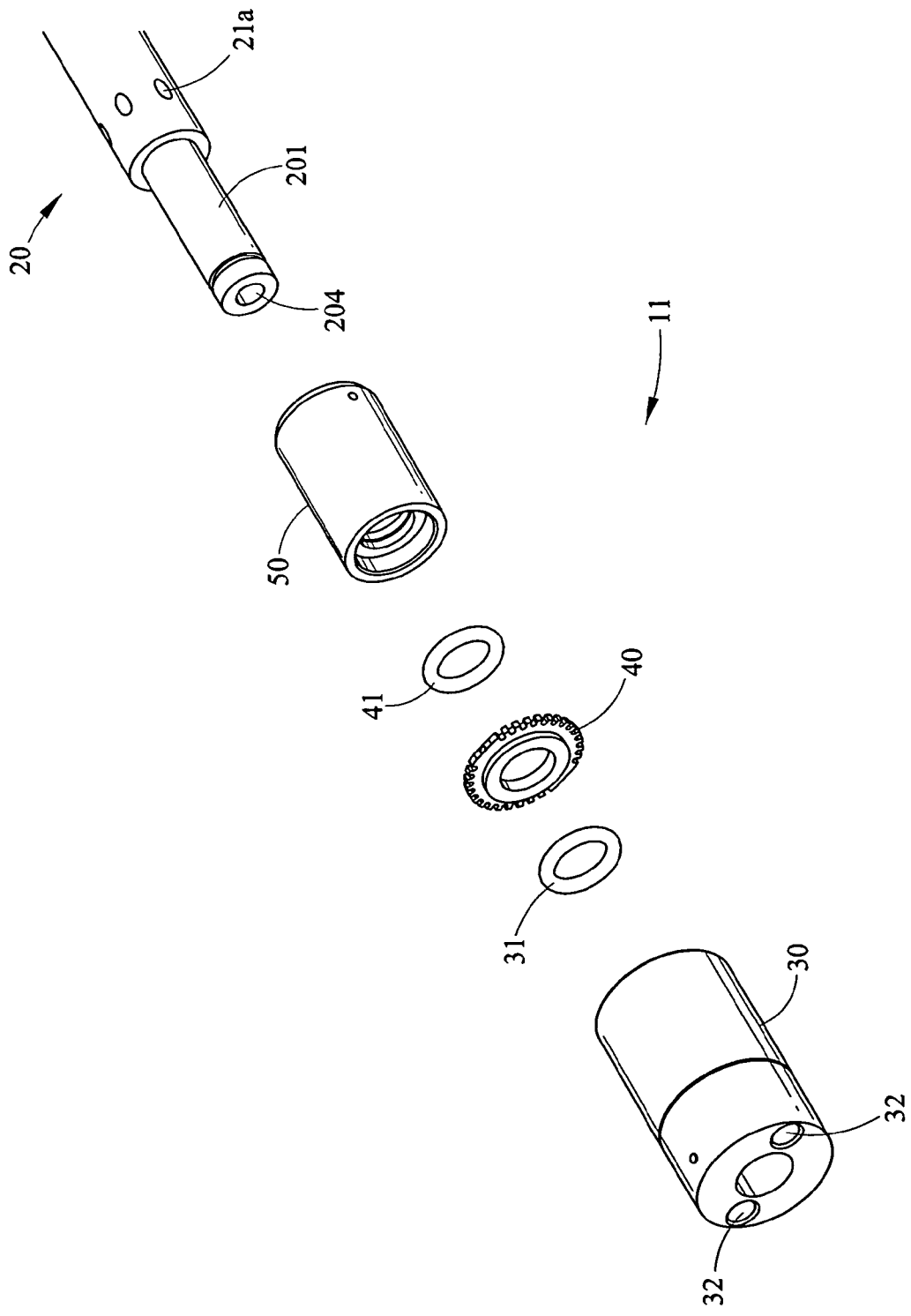
FIG. 3C is an exploded perspective view of the inlet end of the channel shown in FIG. 3B.
Figure 3D:
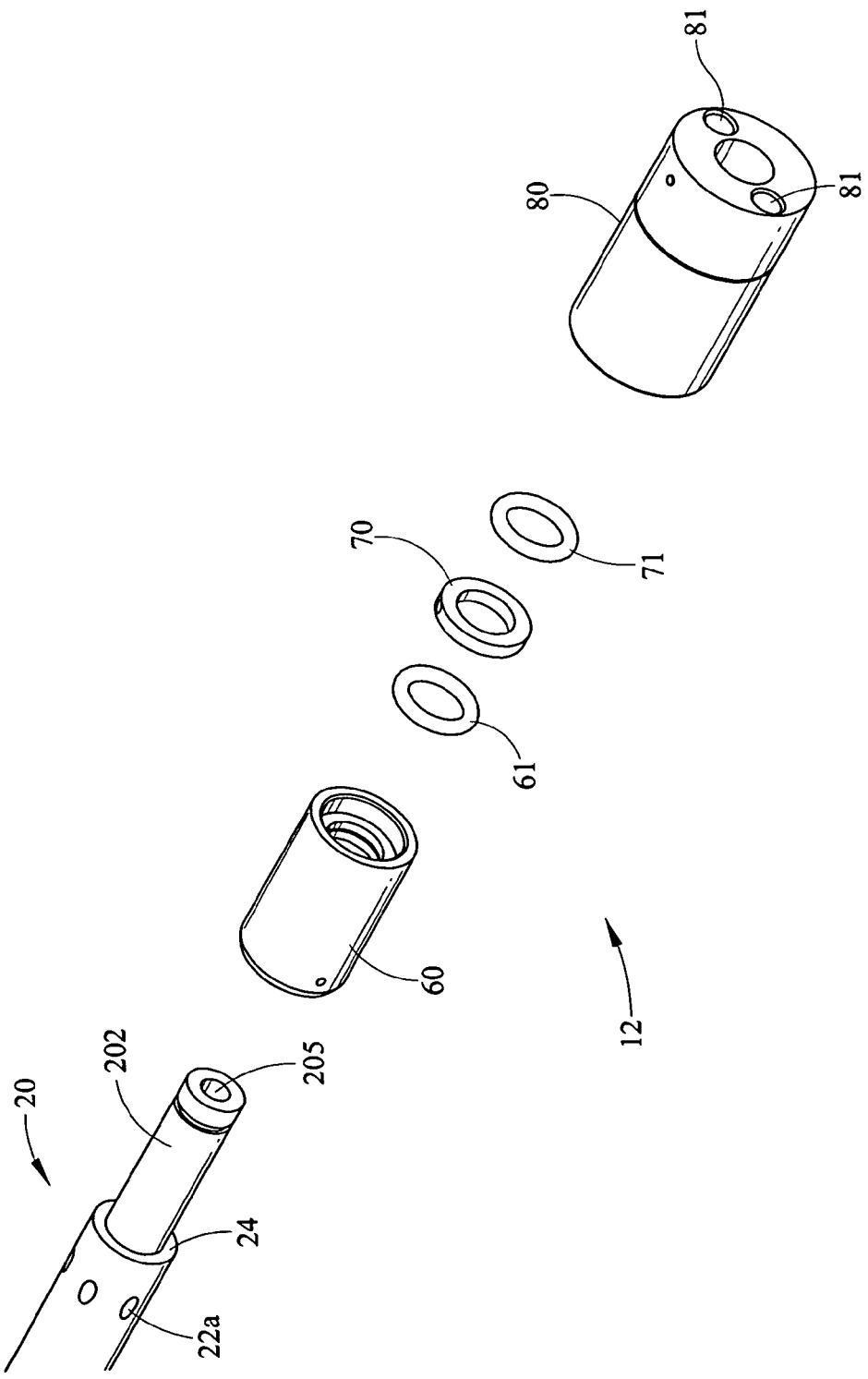
FIG. 3D is an exploded perspective view of the outlet end of the channel shown in FIG. 3B.
Figure 4:
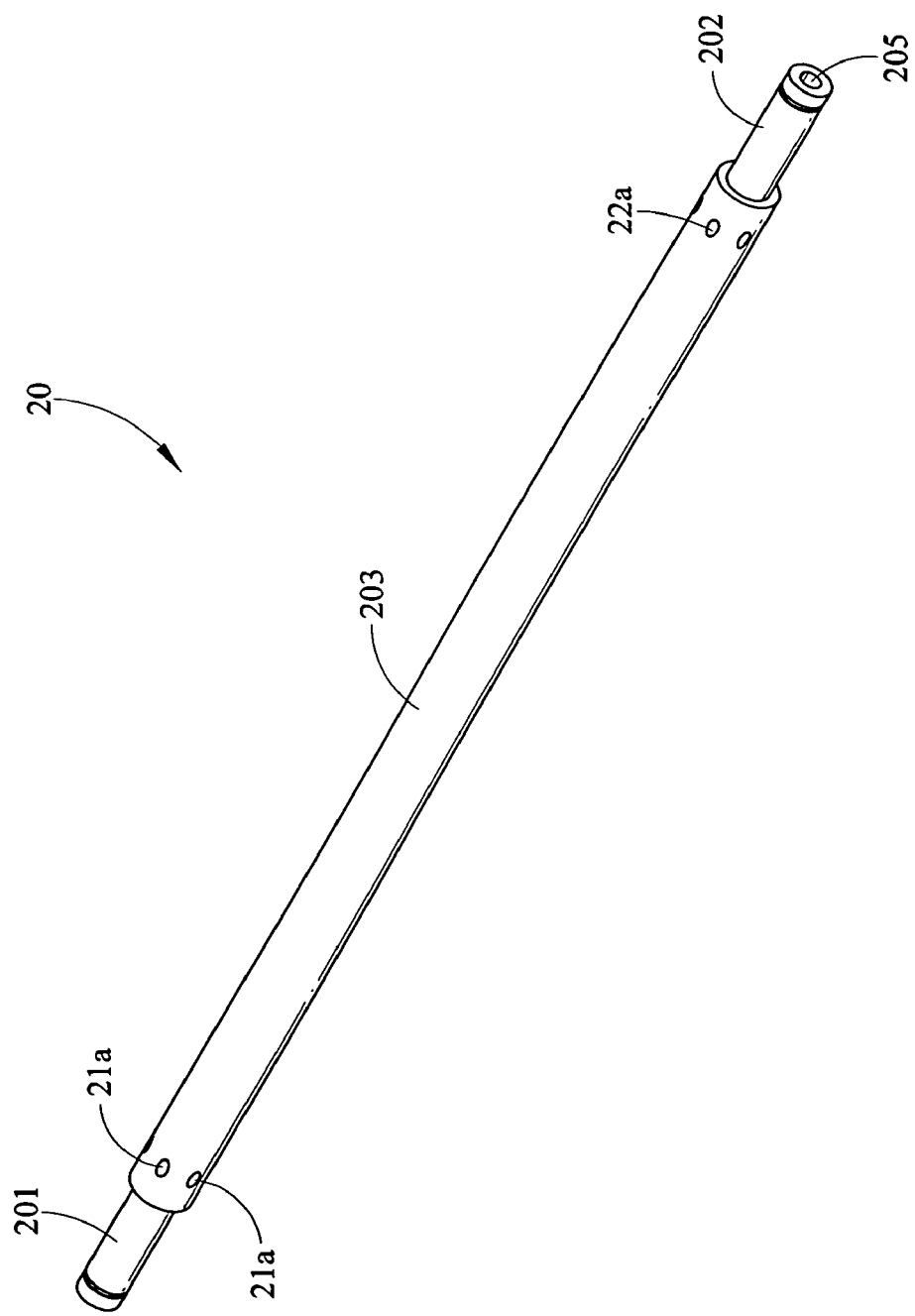
FIG. 4 is a perspective view of a core according to an embodiment of the invention.

Referring now to FIGS. 3A, 3B, 3C, and 3D, an embodiment of the present invention is shown that solves the problems with the prior art devices. FIG. 3A is a section view of an assembled separation flow channel 10. FIG. 3B shows an exploded perspective view of the flow channel 10. FIG. 3C shows an exploded perspective view of the inlet end of the flow channel 10. The flow channel 10 comprises an inlet end 11 and an outlet end 12. The inlet end 11 of the flow channel 10 according to the depicted embodiment comprises a core 20, an inlet adaptor 30, an O-ring 31 that seals the fluid from leaking out of the flow channel 10, a flow distributor 40, an O-ring 41 that prevents mixing of the sample and carrier in the inlet, and an inlet splitter 50. In the middle portion of the flow channel 10 is the core 20 (having an inlet end 21 and an outlet end 22) and the shell 26, which contain the annular flow section 27 where the field is applied and the separation physically takes place. FIG. 3D shows an exploded perspective view of the outlet end 12 of the flow channel 10 according to one embodiment of the invention. The outlet end 12 of the flow channel 10 comprises the outlet end 22 of the core 20, an outlet splitter 60, an O-ring 61 that prevent the separated fractions from mixing, a spacer 70, an O-ring 71 that prevents leakage out of the channel, and an outlet adaptor 80.

Preferably the flow channel 10 comprises a sterile, disposable, closed system flow channel. In the embodiments shown in the figures, the flow channel 10 is primarily comprised of a solid cylindrical core 20 that is concentric with an external cylindrical shell 26, creating the annular flow section 27. The core 20 is approximately 9.32 mm in diameter and 230 mm long. Referring again to FIG. 2, two concentrically aligned fluids (termed a' and b') enter the annular area flow section 27. The feed substream a' enters via feed tube 13 while the carrier substream b' enters via carrier tube 14. The substreams a' and b' are brought together at the tip of the inlet splitter 50 (in the embodiments shown, the inlet splitter 50 is a cylindrical wall) that initially unites the two flows. The fluids then form a fluid-fluid interface and travel in the same direction along the length of the flow channel 10 between the core 20 and the shell 26. The fluids are maintained in the laminar flow regime to prevent turbulence and mixing of the fluids. The fluids then diverge into two separate cylindrical flow paths, with outer flow fraction a exiting via fraction a exit tube 93 and outer flow fraction b exiting via fraction b exit tube 94, at the outlet end 12 of the flow channel 10 by a cylindrical surface (shown as the outlet splitter 60) that lies between the core 20 and the shell 26.

Referring again to FIGS. 2 and 3, initially the solution containing the material that is to be separated is delivered into the top center inlet port, or a'. The interface between the a' and b' fluids forms a theoretical zone called the transport lamina 23. Particles with associated magnetophoretic mobilities travel towards the shell 26 and must cross the thickness of the transport lamina 23 in order to be isolated into the outer flow fraction b at the outlet end 12 of the flow channel 10. Any material, whether it is magnetic or not, that does not cross the plane of the Outlet Splitting Surface (OSS) is maintained in the inner flow fraction a at the outlet end 12 of the flow channel 10. Since the geometry and the magnetic field are static and fixed, the control for the separation process lies with the four flow rates: Qa', Qb', Qa, and Qb.

Assuming that the flow channel geometry, magnetophoretic mobility profile of the sample, and magnetic field strength and geometry are fixed parameters, the entire separation process is defined by three variables that are controlled by the user. The total flow rate, or $Q_{total}$, for the separation process is defined by the following equation:

$$Q_{total} = Qa' + Qb' = Qa + Qb$$

The inlet flow is then characterized by the inlet ratio, $R_i$, defined as:

$$R_i = \frac{Qa'}{Q_{total}}$$

and the outlet flow is characterized by the outlet ratio, $R_o$, defined as:

$$R_o = \frac{Qa}{Q_{total}}$$

By assuming that the flow channel is a fixed volume, these three parameters ($Q_{total}$, $R_i$, and $R_o$) can be used to calculate the four flow rates Qa', Qb', Qa, and Qb.

Referring now to FIGS. 3B, 3C, 4, 7, and 8, details of the depicted core are provided. The core comprises three concentric cylindrical sections, a first cylinder 201 at the inlet end 21, a second cylinder 202 at the outlet end 22, and a third cylinder 203 having a larger diameter that connects the first and second cylinders 201, 202. The first cylinder 201 comprises an axial sample inlet port 204 to admit the sample a' into the flow channel 10. Near the junction between the first cylinder 201 and the third cylinder 203 are multiple sample dispersion ports 21a. The multiple sample dispersion ports 21a allow the sample a' to surround the core 203, thus admitting the sample flow a' into an annular space between the core 203 and the inlet splitter 50 (described below). This converts the sample a' flow into a substantially circumferentially uniform, annular flow geometry. Note that in the embodiment shown, the sample dispersion ports 21a radiate the sample flow at an angle to the longitudinal axis of the flow channel 10 (see, e.g., FIG. 3A). Preferably, the internal geometry of the outlet end of the core 20 (that is, second cylinder 202) is a mirror image of the geometry at first cylinder 201. Near the junction of the third cylinder 203 and the second cylinder 202 are multiple ports 22a that convert the negatively selected fraction a from a circumferentially uniform, annular flow geometry to a cylindrical flow geometry. At the outlet end 22 an outlet port 205 discharges this negatively selected fluid portion a. In additional embodiments not specifically shown in the figures, the radiating fluid paths could also be positioned perpendicularly to the axis of the channel, or even in several other physical configurations.

The primary function of the inlet adaptor 30 is to introduce the carrier b' fluid into the flow channel 10. Likewise, the primary function of the outlet adaptor 80 is to elute fraction b from the flow channel 10. The inlet adaptor 30 and outlet adaptor 80 are preferably identical. The adaptors 30, 80 in the embodiment shown, each provide one or more carrier inlet ports 32 where standard tubing (carrier tube 14) is inserted and bonded in place. This tubing interface creates a sealed fluid connection at the inlet for the carrier b' to enter the plenum between the inlet adaptor 30 and flow distributor 40, or at the outlet for fraction b to pass from the plenum between the outlet splitter 60 and the outlet adaptor 80 to the tubing 94 exiting the flow channel 10 via tubing ports 81. Furthermore, the inlet adaptor 30, together with the outlet adaptor 80, physically supports and positions the shell 26 concentrically to the core 20. Additionally, each adaptor 30, 80 comprises an O-ring groove that accepts the outermost O-ring 31, 71 (O-ring 31 at the inlet, O-ring 71 at the outlet), which prevents any fluid from passing between the adaptor 30, 80 and core 20 and thus prevents any leakage along the core 20 and out of the flow channel 10.

Figure 5B:
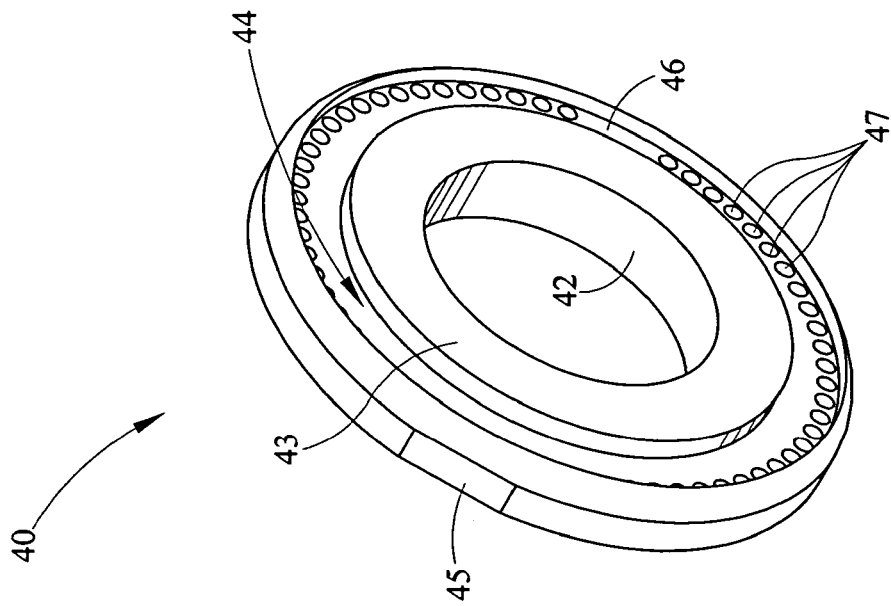
FIG. 5B is a perspective view of a second embodiment of a flow distributor according to the invention.
Figure 5A:
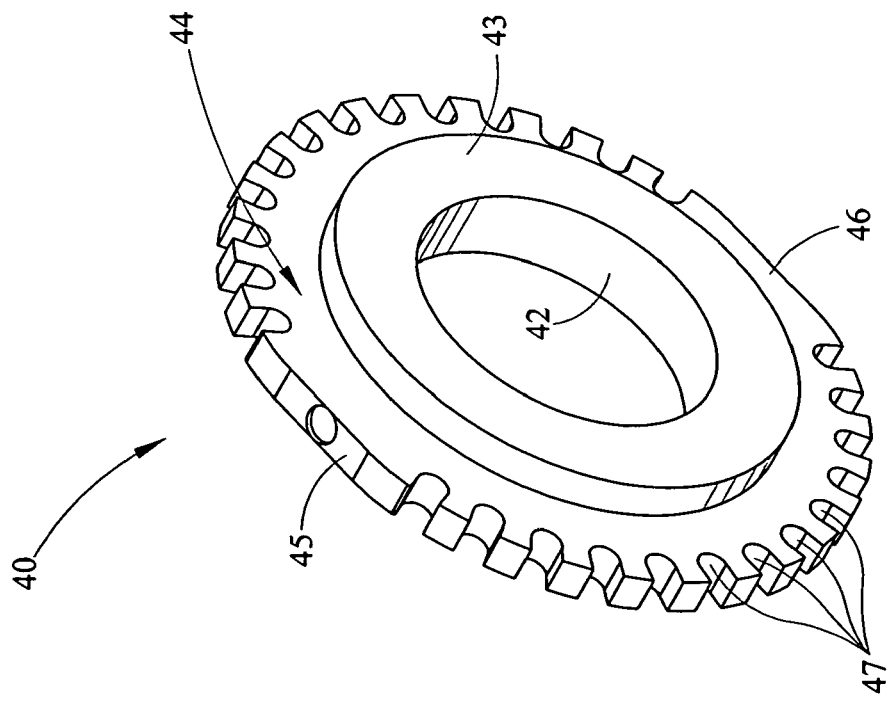
FIG. 5A is a perspective view of an embodiment of a flow distributor according to the invention.

As described above, the core 20 is the structure that deflects the sample flow a' into its preferred circumferentially uniform annular geometry. In the embodiment shown, a flow distributor 40 deflects the carrier flow b'. FIGS. 5A and 5B depict perspective views of two embodiments of the flow distributor 40. The flow distributor 40 deflects one or more cylindrical inlet carrier flows b' to a laminar, circumferentially uniform, annular geometry. For both embodiments shown, the flow distributor 40 comprises an alignment surface 42 that positions the flow distributor 40 relative to the core 20, a central support hub 43, a fluid distribution plenum 44, a keyed alignment feature 45 that aligns the initial fluid flow with a blocked flow path 46, and a plurality of fluid ports 47. The alignment surface 42 provides a means for aligning the flow distributor 40 concentrically around the core 20 and the alignment feature 45 provides a means for aligning the flow distributor 40 rotationally with the inlet adaptor 30 so that the b' flow flows in from the adaptor 30 onto a closed section of the flow distributor instead of directly into the fluid ports 47. The plurality of fluid ports 47 preferably provide parallel flow paths. This arrangement is somewhat akin to a showerhead concept. The multiple parallel paths of the fluid ports 47 are the key to a circumferential distribution of the fluid. The keyed alignment feature 45 ensures that the flow from the inlet adaptor 30 does not have a direct path into the flow channel 10. Instead, the flow from the inlet adaptor 30 is directed onto the blocked flow path 46 of the flow distributor 40, which deflects the flow into the plenum 44 volume and around the circumference of the flow channel 10.

Figure 6A:
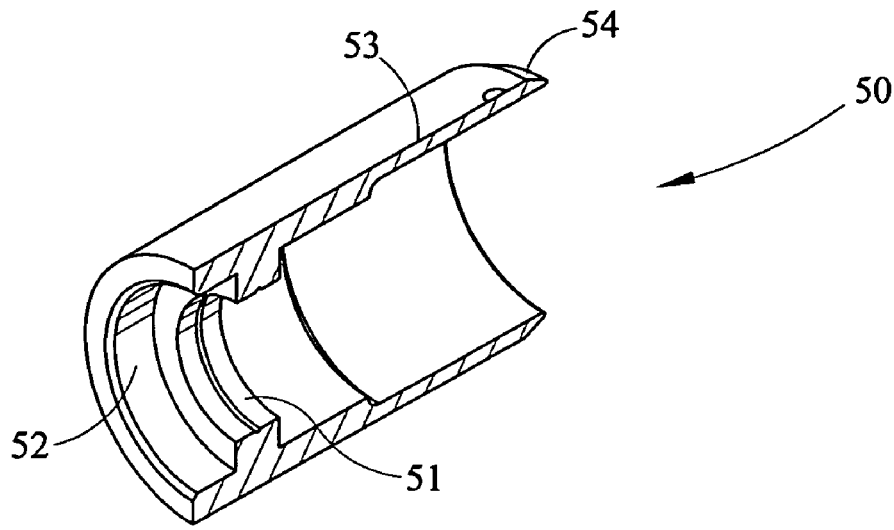
FIG. 6A is a perspective sectional view taken along section 6A of FIG. 6C of a splitter according to an embodiment of the invention.
Figure 6B:
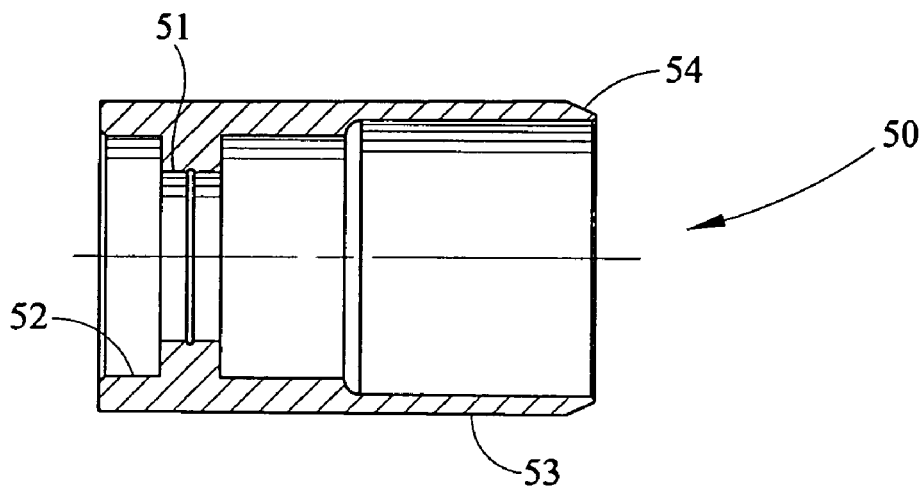
FIG. 6B is a side elevation sectional view taken along section 6B of FIG. 6C of the splitter shown in FIG. 6A.
Figure 6C:
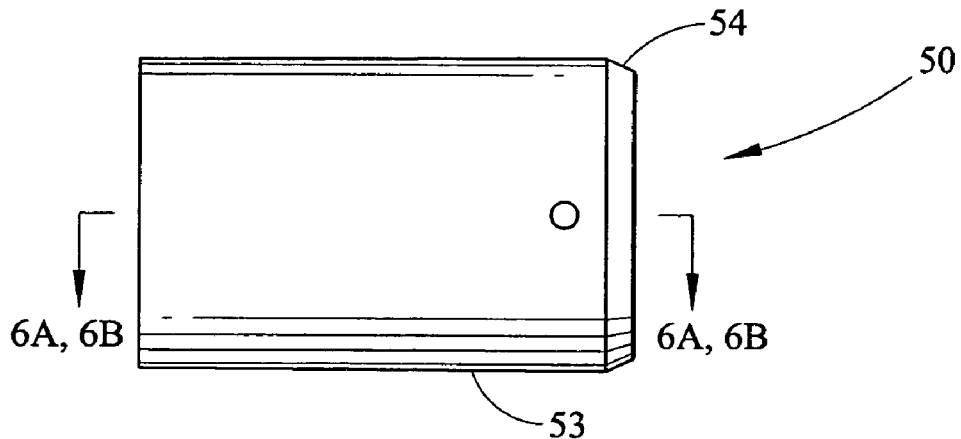
FIG. 6C is a side elevation view of the splitter shown in FIG. 6A.
Figure 7:
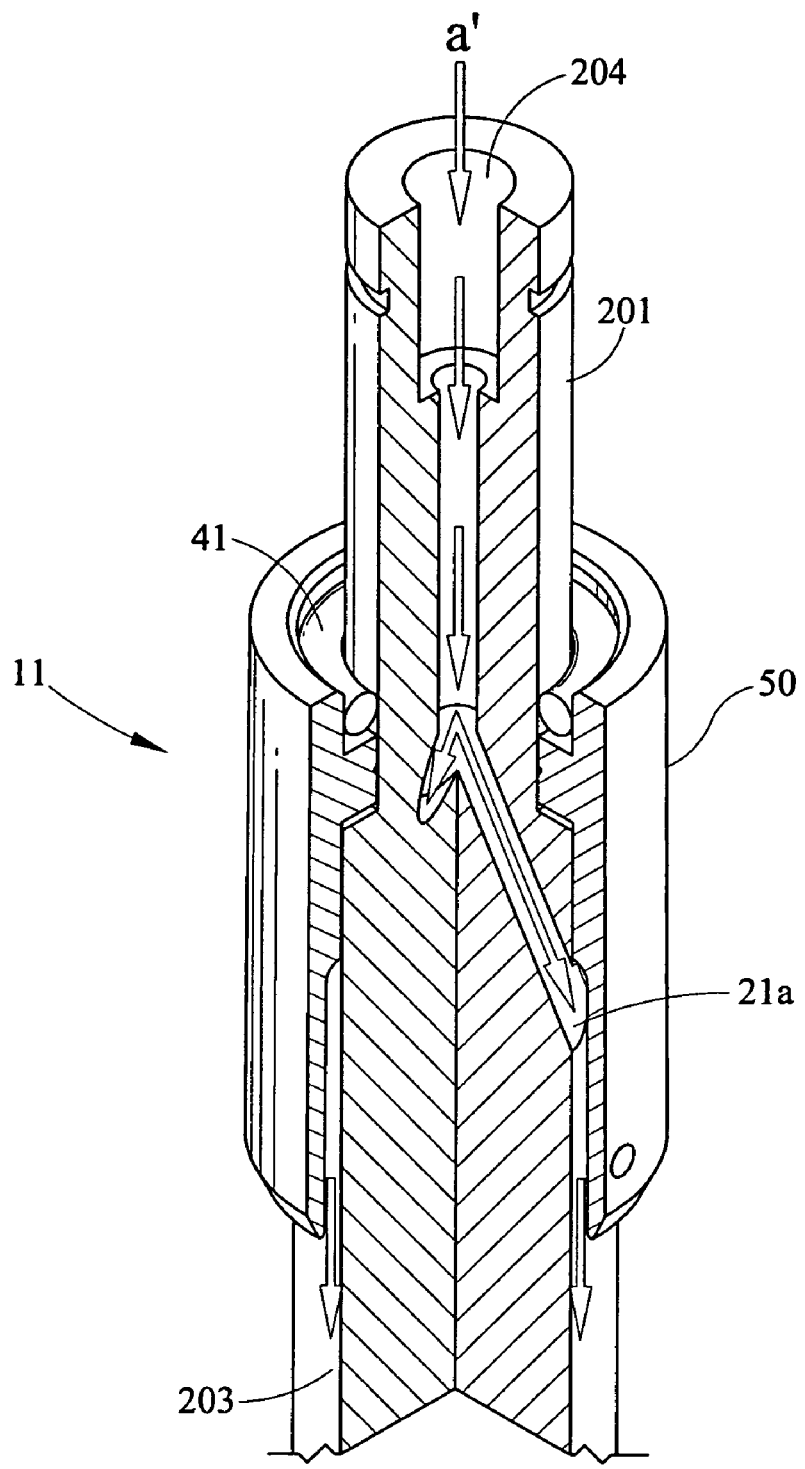
FIG. 7 is a perspective view in partial section of the inlet end of the channel showing the geometric relationship between the core and the inlet splitter according to an embodiment of the invention.
Figure 8:
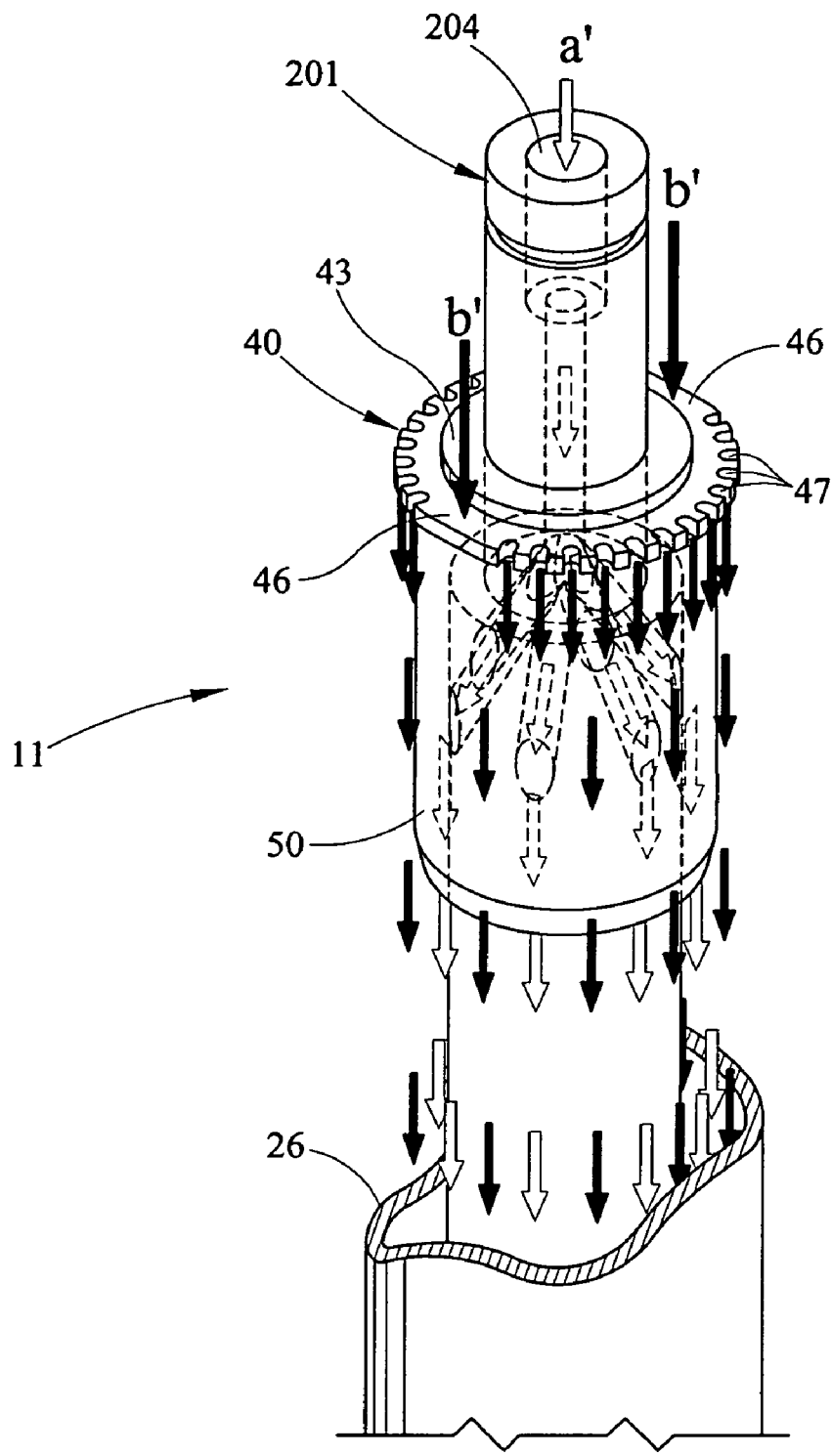
FIG. 8 is a perspective view of the inlet end of the channel having a flow distributor attached thereto, showing the geometric relationship between the core, the inlet splitter, the flow distributor, and the shell according to an embodiment of the invention.

Referring now to FIGS. 6A, 6B, 6C, and again to FIG. 3C, an inlet splitter 50 according to an embodiment of the invention is presented. The inlet splitter 50 is substantially cylindrical, having a cylindrical wall 53. The inlet splitter 50 further comprises an alignment surface 51 that positions the inlet splitter 50 relative to the 20 core. With reference also to FIGS. 7 and 8, the inlet splitter 50 further comprises an O-ring groove 52 that permits the installation of the O-ring 41 that seals the two fluid compartments to prevent mixing of the sample a' and carrier b' at the inlet. Likewise, O-ring 61 seats in the outlet splitter 60 to prevent mixing of the two fractions a, b. This means that the sample a' and the carrier b' are completely separate flows across the length of the inlet splitter 50, and they do not come into contact until they flow past the inlet splitter 50. The cylindrical wall 53 is designed to isolate the two annular fluid volumes (the sample a' and carrier b') at the inlet, and a similar structure in the outlet splitter 60 isolates the negatively selected a and positively selected b fractions at the outlet. The cylindrical wall 53 terminates at a chamfered tip 54 that minimizes any disturbances at the fluid-to-fluid interface in the inlet and outlet. The inlet splitter 50 provides the fluid-to-fluid contact point where the sample a' and carrier b' form a single stable laminar annular flow.

The outlet splitter 60 is of similar design to the inlet splitter 50. The outlet splitter 60 provides the dividing point that splits the single annular flow from the transport lamina region 23 into the two outlet fractions, a and b. Typically, the diameter of the inner wall 53 is different between the inlet and outlet splitters 50, 60 in order to optimize the flow channel 10 for specific inlet and outlet flow ratios, respectively (the inner diameter is larger for high flow ratios and smaller for lower flow ratios, and can generally be set for flow ratios from 0.1 to 0.4). For identical inlet and outlet flow ratios, the inlet and outlet splitters 50, 60 could be considered interchangeable.

Referring now to FIGS. 7 and 8, and with continuing reference to FIGS. 3C, 5A, and 5B, a better representation of the assembly at the inlet end 11 of the flow channel 10 is shown. The cylindrical face of the core 201 at the inlet end 11 provides an alignment datum that is common to all of the inlet components and maintains a tight concentric alignment of the parts. The inlet adaptor 30, inlet splitter 50, and flow distributor 40 at the inlet end 11 of the flow channel 10 are concentrically aligned with the annular flow section by mating internal cylindrical faces for each of these parts against the cylindrical alignment datum at the inlet end 21 of the core 20. The inlet end 21 of the core 20, due to the configuration of the first cylinder 201 and the third cylinder 203, comprises a face 24 that is perpendicular to the cylindrical axis and provides a physical datum that axially positions the inlet components. The outlet end 12 of the flow channel 10 is configured as a mirror image to the inlet end 11 of the flow channel 10, except that the flow distributor 40 is replaced by a spacer 70 that provides the same axial positioning of the components as at the inlet.

Referring again to FIG. 7, the positioning of the inlet splitter 50 on the core 20 is shown. The inlet splitter 50 is positioned concentrically on the core 20 due to the cylindrical mating surfaces of the core 20 and inlet splitter 50, and the inlet splitter 50 is located axially on the 20 core by the mating of the female shoulder in the splitter against the male shoulder on the core. The annular volume between the inlet splitter 50 and the core 20 contains the sample solution a'. The O-ring 41 seals the sample a', which flows inside of the inlet splitter 50, from the carrier b', which flows outside of the inlet splitter 50.

Referring again to FIG. 8, the flow distributor 40 is shown positioned onto the inlet splitter 50. The fluid path for the carrier b' is apparent in this view, which displays the plurality of fluid ports 47 where the carrier can flow through the flow distributor 40 and down the outside of the inlet splitter 50. The flow distributor 40 is positioned concentrically on the core 20 due to the cylindrical mating surfaces of the core 20 and flow distributor 40, and the flow distributor 40 is located axially on the core 20 by the mating of the bottom face of the flow distributor 40 against the top face of the inlet splitter 50. The annular flow zone between the adaptor and the inlet splitter 50 just downstream of the flow distributor 40 provides a means for providing a circumferentially consistent axial laminar flow.

Figure 9A:
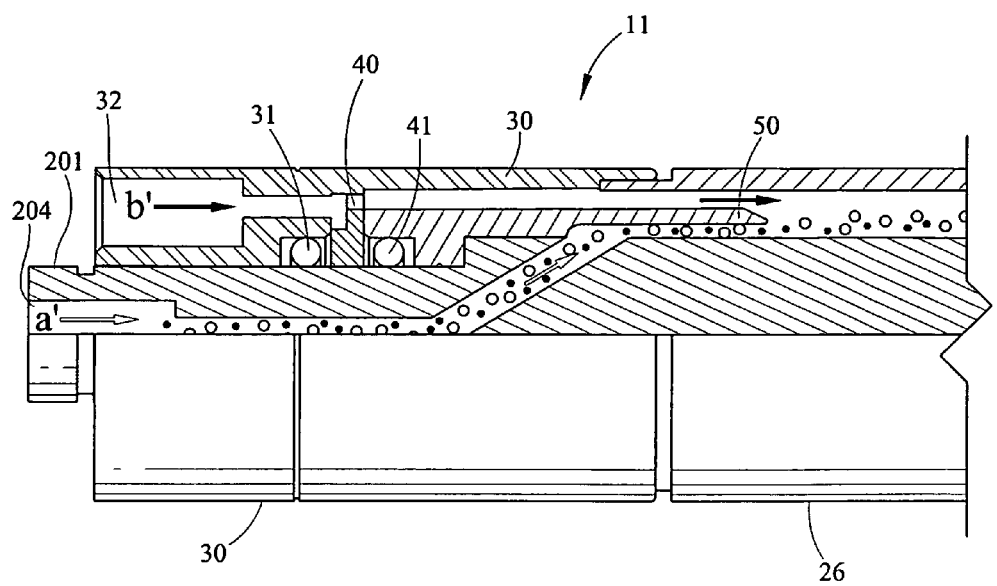
FIG. 9A is a quarter section view of the inlet end of an assembled flow channel according to an embodiment of the invention.
Figure 9B:
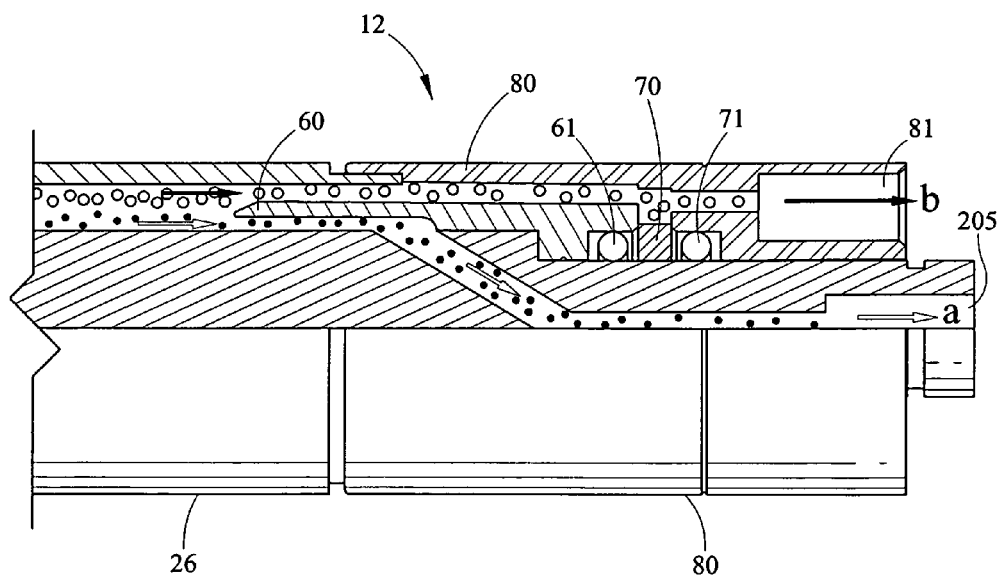
FIG. 9B is a quarter section view of the outlet end of an assembled flow channel according to an embodiment of the invention.

Referring now to FIG. 9A, a quartered section of the flow channel 10 inlet end 11 is shown for additional clarification of flow paths inside the flow channel 10. This view shows the inlet adaptor 30, O-rings 31, 41, flow distributor 40, inlet splitter 50, core 20, and shell 26. Note that all parts with the exception of the shell 26 are physically centered on the core 20. Both the carrier inlet ports 32 in the inlet adaptor 30 and the sample inlet port 204 in the core 20 (in communication with feed tube 13) are also displayed in this view. Similarly, in FIG. 9B, a quartered section of the flow channel 10 outlet end 12 is shown. During assembly, special fixtures (not shown) are used to clamp the flow channel parts along the long axis of the flow channel 10 while adhesive is applied to the joint between the shell 26 and the inlet adaptor 30. Once the adhesive is set, then all components are fixed in position in the flow channel 10. Flexible tubing is adhesively bonded into the inlet adaptor 30 and core 20 at the fluid ports. Additional obvious joining methods which may be used as a replacement to adhesive bonding exist, such as ultrasonic welding or solvent bonding the pieces together.

Figure 10:
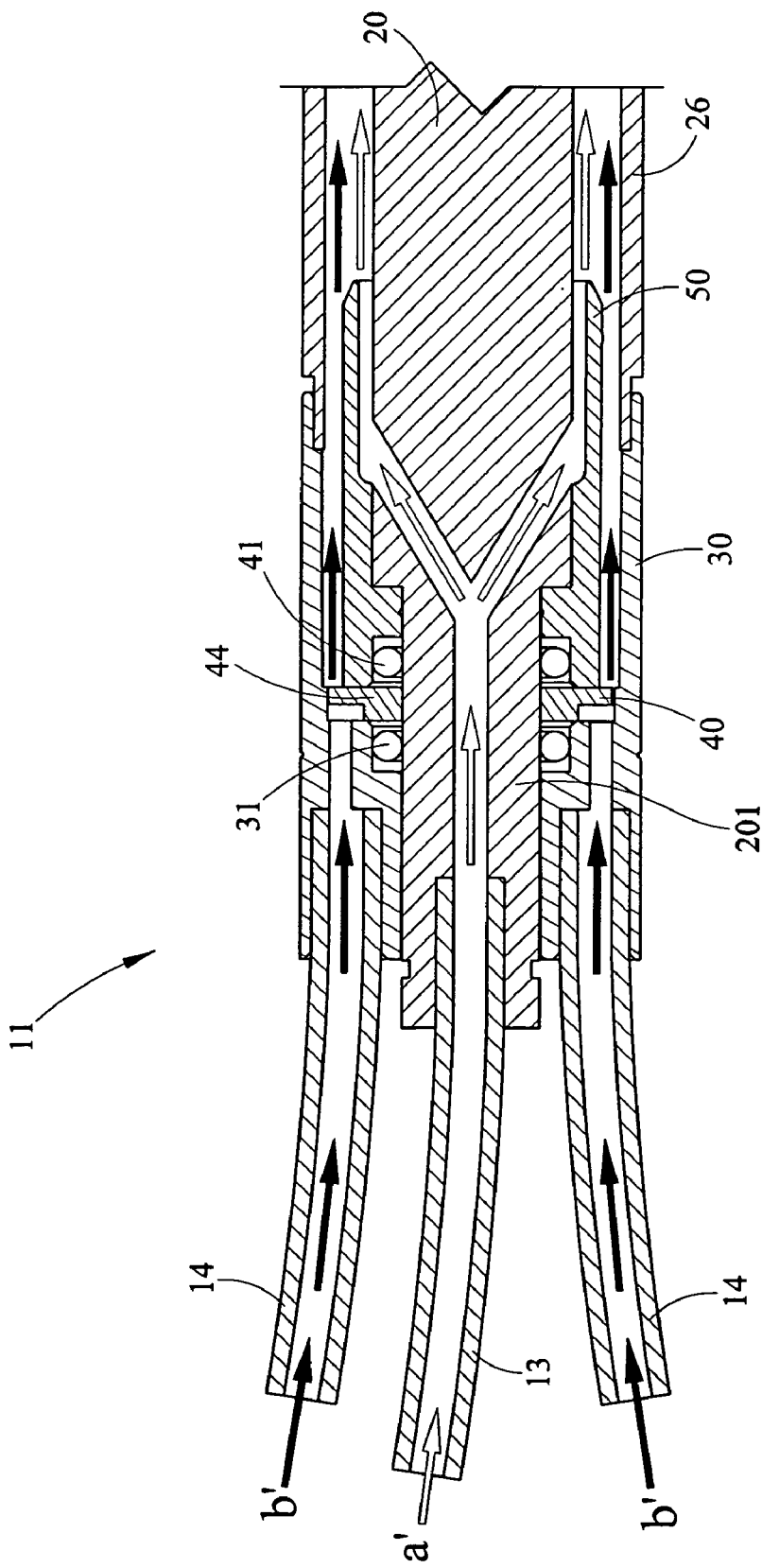
FIG. 10 is a sagittal-sectional view of the inlet end of an assembled flow channel according to an embodiment of the invention showing the flow path down the center of the core for the sample (a') and showing the blocked plenum flow for the carrier fluid (b')
Figure 11:
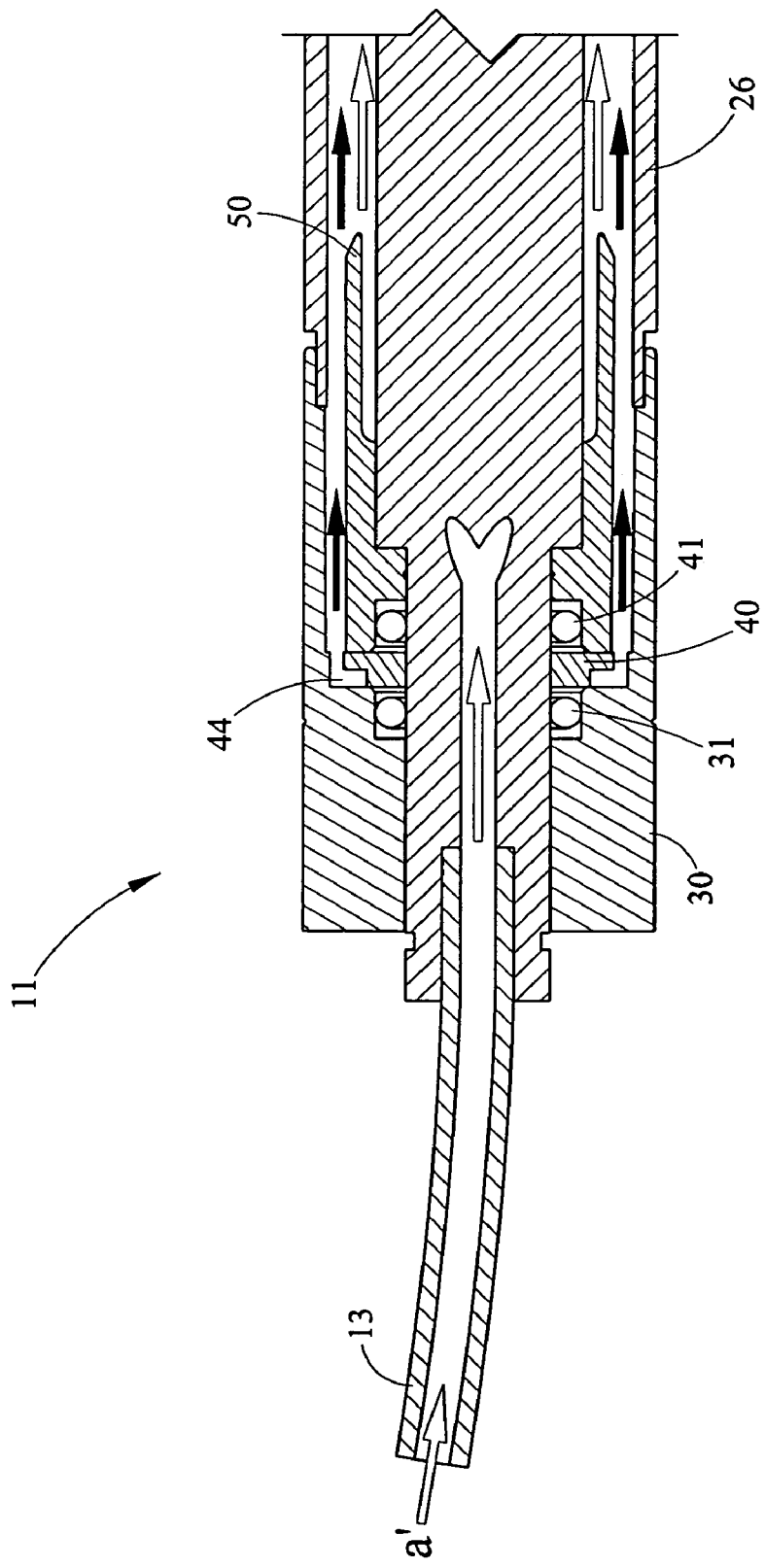
FIG. 11 is a sagittal-sectional view of the inlet end of an assembled flow channel according to an embodiment of the invention showing the fluid path from the blocked plenum flow for the carrier fluid (b') into the annular flow volume.

FIGS. 10 and 11 display sagittal sections of the assembled flow channel 10 according to one embodiment of the invention, taken at 90 degree positions relative to one another. In FIG. 10, with continuing reference to FIG. 3C, the inlet splitter 50, together with the inlet end 21 of the core 20, provides the annular flow region where the sample fluid a' develops into a stable laminar annular flow. In this sagittal sectional view, the entry of the carrier fluid b' shows where the carrier enters into the fluid distribution plenum 44, which is located between the flow distributor 40 and the inlet adaptor 30. The flow then distributes circumferentially around the channel 20. FIG. 11 shows a sagittal section at one of the fluid paths through the flow distributor 40. The carrier b' flows through the flow distributor 40 and then enters the annular region between the inlet splitter 50 and the inlet adaptor 30. The inlet splitter 50, together with the inlet adaptor 30, provides the annular flow region where the carrier fluid b' develops into a stable laminar annular flow.

Figure 12:
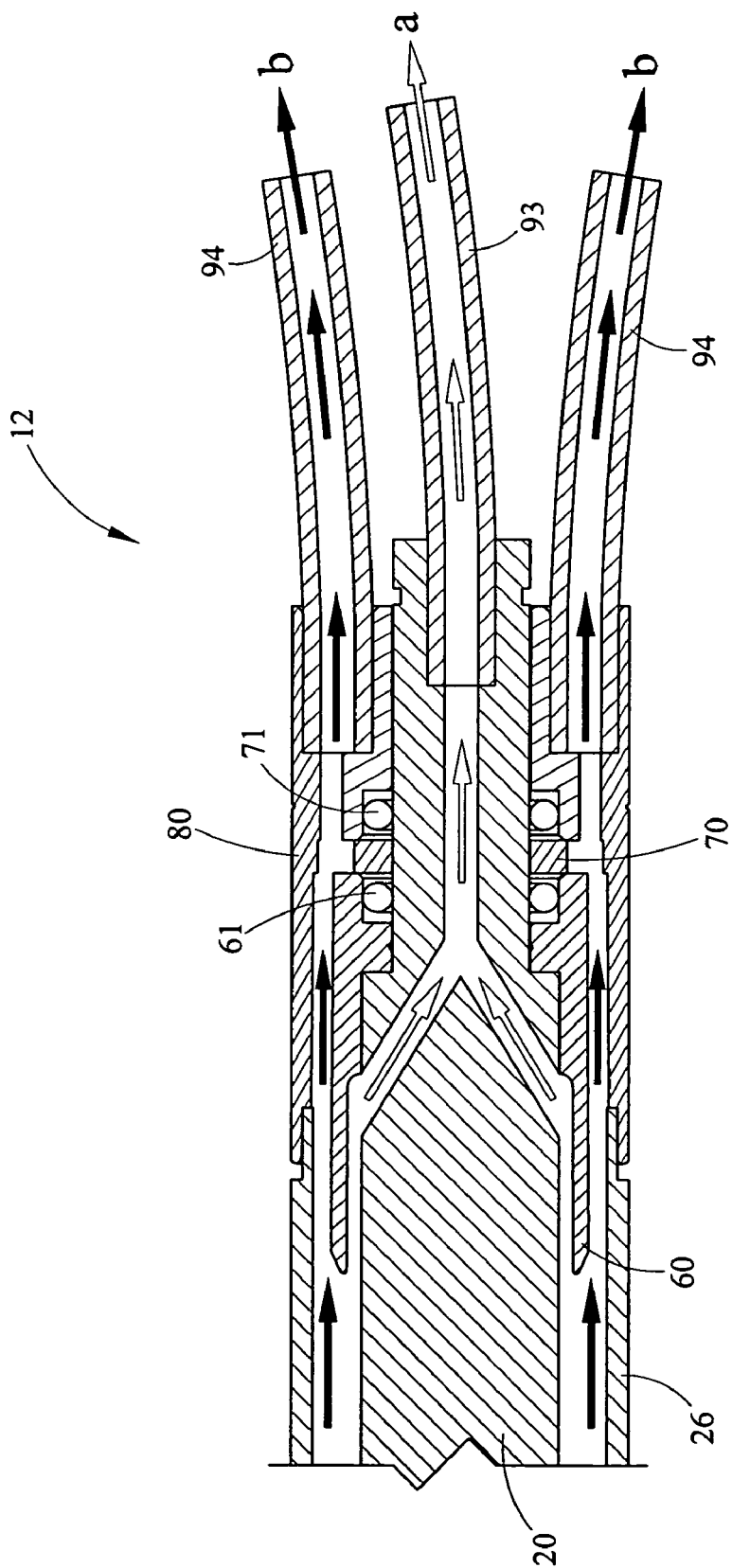
FIG. 12 is a sagittal-sectional view of the outlet end of an assembled flow channel according to an embodiment of the invention showing the fluid path for the two separated fractions (a and b)

Referring now to FIG. 12 and again to FIG. 3D, a sagittal sectional view of the outlet end 12 of the flow channel 10 is shown. The outlet splitter 60, together with the outlet adaptor 80, provides the annular flow region where the selected fraction b transitions from a single laminar annular flow into the plurality of flow paths going into the ports in the outlet adaptor 80. Furthermore, the outlet splitter 60, together with the outlet end 22 of the core 20, provides the annular flow region where the non-selected fraction a transitions from a single laminar annular flow into the plurality of fluid paths going into the ports in the core.

Figure 13:
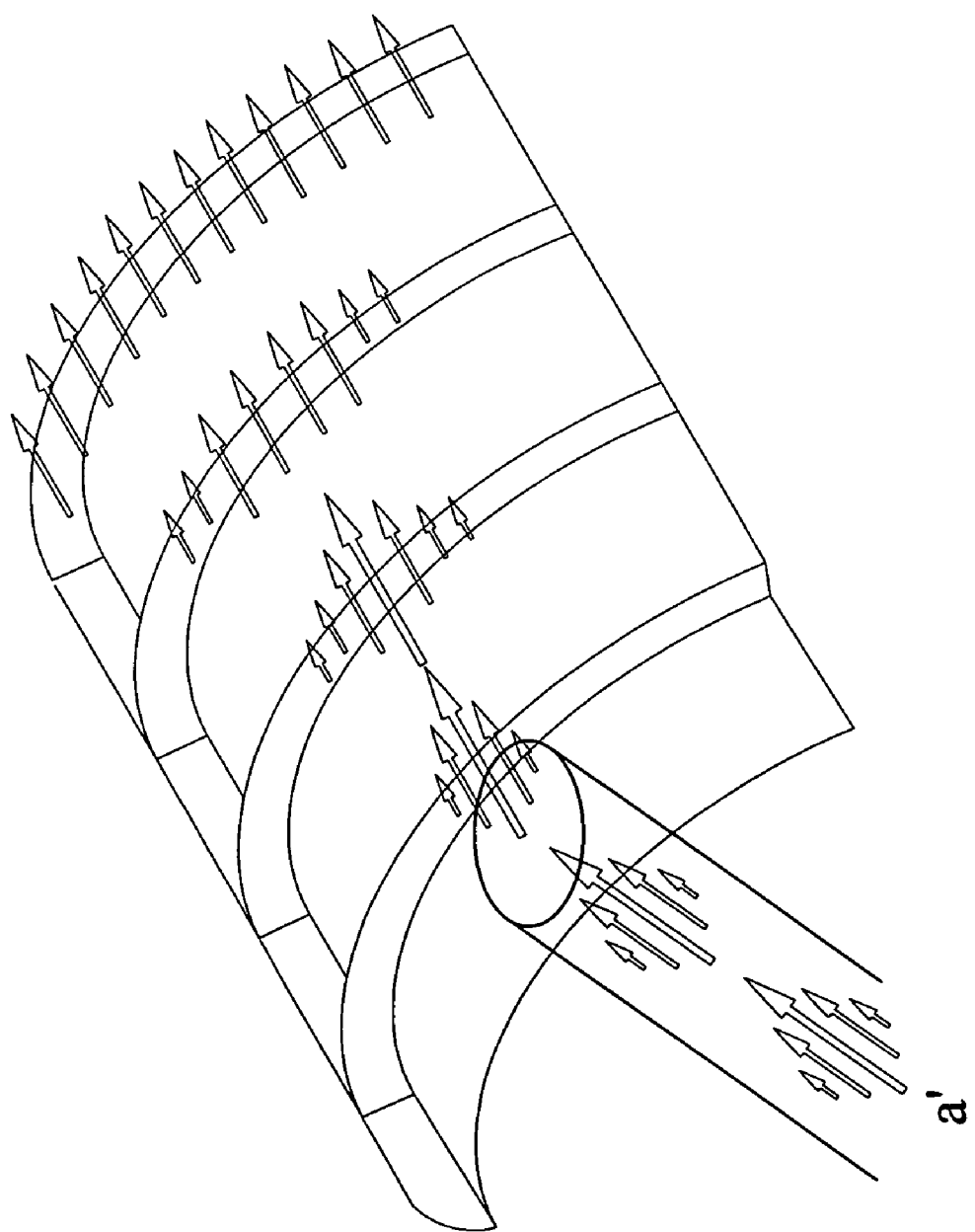
FIG. 13 is a streamline diagram showing the distribution of the sample flow (a') from one of the fluid ports in the core to the fully developed, circumferentially consistent annular flow at the splitter tip.

FIG. 13 displays a section of the flow channel 10 inlet showing the even distribution of flow of the sample a' from the core 20 to the inner wall 53 of the inlet splitter tip 54 via streamlines that approximate the results calculated by computational fluid dynamics methods. Note that the flow paths are very uniform and consistent over the entire circumference of the figure at the splitter tip, which is an improvement over the prior art.

Figure 14:
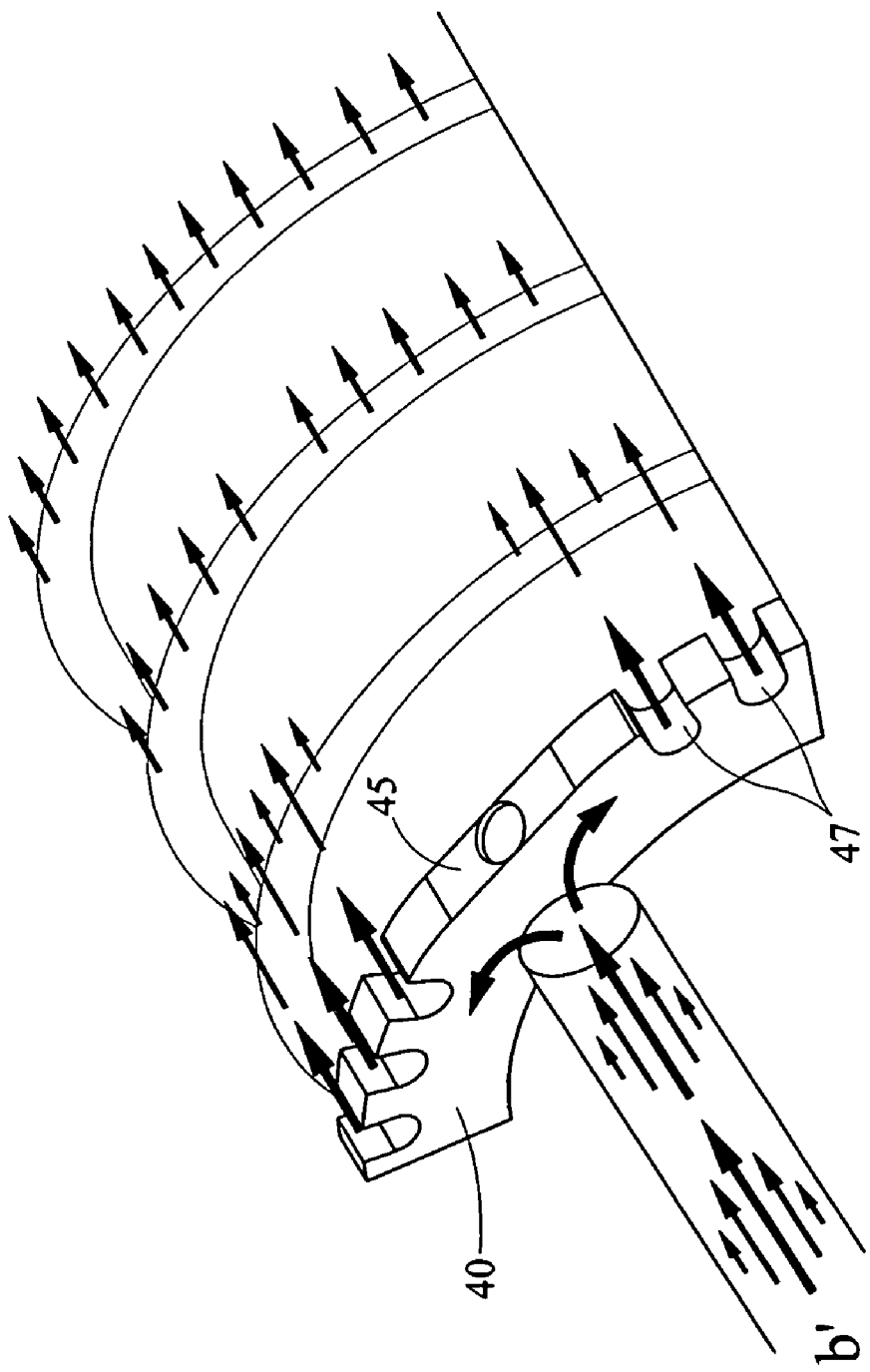
FIG. 14 is a streamline diagram showing the distribution of the carrier flow (b') from one of the adaptor ports, through the flow distributor, to the fully developed, circumferentially consistent annular flow at the splitter tip.

FIG. 14 displays a section of the flow channel 10 inlet showing the even distribution of flow of the carrier b' from the inlet adaptor 30, through the flow distributor 40, to the outer wall 53 of the inlet splitter tip via streamlines that approximate the results calculated by computational fluid dynamics methods. Note that the flow paths are very uniform and consistent over the entire circumference of the figure at the splitter tip, which is an improvement over the prior art.

While there has been described and illustrated particular embodiments of the fluid distribution and assembly features of a split-flow thin separation channel, it will be apparent to those skilled in the art that variations and modifications may be possible without deviating from the broad spirit and principle of the present invention, which shall be limited solely by the scope of the claims appended hereto.

What is claimed is:

1. A flow channel for use with dispensing apparatus dispensing a sample flow and a carrier flow, said flow channel capable of developing a circumferentially consistent, laminar, annular separation flow for a range of inlet and outlet flow ratios, said flow channel comprising:
   (a) a core having an inlet end and an outlet end and a cylindrical wall;
   (b) a cylindrical shell having an inlet end and an outlet end and a cylindrical wall, wherein said cylindrical wall has a diameter larger than that of said cylindrical wall of said core and being concentrically aligned with said core, creating an annular flow volume;
   (c) an inlet adaptor connecting said carrier flow to said channel;
   (d) a flow distributor that deflects said carrier flow to a laminar, circumferentially uniform, annular flow;
   (e) an inlet splitter providing a contact point for said sample flow and said carrier flow;
   (f) an outlet splitter converting said sample flow and said carrier flow into a positively selected outlet fraction and a negatively selected outlet fraction; and
   (g) an outlet adaptor for separately conveying one of said positively selected outlet fraction and said-negatively selected outlet fraction for further use.

2. The flow channel of claim 1 wherein said core further comprises a first cylindrical body at said inlet end of said core, a second cylindrical body at said outlet end of said core, and a third cylindrical body therebetween having a diameter larger than that of said first and second cylindrical bodies.

3. The flow channel of claim 2 wherein said first cylindrical body mates with and coaxially aligns said inlet adaptor, said flow distributor, and said inlet splitter creating an annular flow volume between said third cylindrical body of said core and said cylindrical shell.

4. The flow channel of claim 3 wherein said second cylindrical body mates with and coaxially aligns said outlet splitter and said outlet adaptor.

5. The flow channel of claim 4 wherein said inlet end of said core further comprises a sample inlet port.

6. The flow channel of claim 5 wherein said third cylindrical body near said inlet end of said core further comprises multiple sample inlet ports.

7. The flow channel of claim 6 wherein said multiple inlet ports inject sample into a first annular region between said core and said inlet splitter.

8. The flow channel of claim 7 wherein said first annular region has a length sufficient to permit said sample to develop into a circumferential substantially consistent axial laminar flow.

9. The flow channel of claim 8 wherein said inlet adaptor further comprises one or more carrier inlet ports that inject said carrier into a plenum area between said inlet adaptor and said flow distributor.

10. The flow channel of claim 9 wherein said flow distributor further comprises a plurality of fluid ports that inject carrier from said plenum into a second annular region between said inlet splitter and said inlet adaptor.

11. The flow channel of claim 10 wherein said second annular region is of sufficient length to permit said carrier to develop into a circumferential substantially consistent axial laminar flow.

12. The flow channel of claim 11 wherein said inlet splitter further comprises an angled taper to minimize mixing of said sample and said carrier, creatine a single circumferentially consistent axial laminar flow.

13. The flow channel of claim 12 wherein said outlet splitter provides an angled taper to divide said single circumferentially consistent axial laminar flow with minimal turbulence.

14. The flow channel of claim 13 wherein a third annular region is created between said outlet splitter and said outlet adaptor that injects positively-selected fluid into one or more tubing ports in said outlet adaptor.

15. The flow channel of claim 14 wherein said third annular region is of sufficient length to minimize upstream turbulence caused by conversion of fluid geometry at said outlet adaptor tubing ports.

16. The flow channel of claim 15 wherein a fourth annular region is created between said outlet splitter and said core that injects negatively-selected fluid into one or more ports in said core.

17. The flow channel of claim 16 wherein said fourth annular region is of sufficient length to minimize upstream turbulence caused by conversion of the fluid geometry at said core.

18. The flow channel of claim 1 wherein said inlet splitter further comprises a splitter tip diameter that matches a calculated Inlet Splitting Surface (ISS) diameter for preselected flow parameters in order to minimize turbulence, compression, or crossover of said inlet sample and said inlet carrier.

19. The flow channel of claim 1 wherein said outlet splitter further comprises a splitter tip diameter that matches a calculated Outlet Splitting Surface (OSS) diameter for preselected flow parameters in order to minimize turbulence, compression, or crossover of said positively selected outlet fraction and said-negatively selected outlet fraction.

20. The channel of claim 18 further comprising multiple inlet splitters that are interchangeable to optimize said flow channel for various flow parameters.

21. The channel of claim 19 further comprising multiple outlet splitters that are interchangeable to optimize said flow channel for various flow parameters.

22. A method for providing circumferentially consistent axial laminar flow of a sample and a carrier in a split-flow thin separation flow channel comprising the steps of:
   providing a core having a stepped cylindrical shape at an inlet end thereof and having therewithin a sample inlet port and one or more sample dispersion ports in communication with said sample inlet port;
   providing an inlet splitter coaxially around said core, said inlet splitter comprising a substantially cylindrical body having an outer wall and an inner wall and a seating surface on said inner wall and wherein said outer wall terminates in a chamfered tip;
   providing a flow distributor comprising a substantially disc-like body having an outer perimeter and a cylindrical opening therein for coaxially mounting on said core of said flow channel, wherein said outer perimeter further comprises a plurality of fluid ports;
   providing one or more O-rings to seat on said seating surface of said inner wall to seal said inner wall around said core;
   providing a sample flow into said core;
   providing a carrier flow into said inlet splitter;
   wherein said sample flows from said sample inlet through said one or more sample dispersion ports in between said core and said inner wall of said inlet splitter, and wherein said carrier flows through said plurality of fluid ports of said flow distributor along said outer wall of said inlet splitter, and wherein said carrier and said sample flow in steady laminar flow upon passing said chamfered tip.

* * * * *